US008545563B2

(12) United States Patent
Brun et al.

(10) Patent No.: US 8,545,563 B2
(45) Date of Patent: Oct. 1, 2013

(54) INTERVERTEBRAL IMPLANT HAVING EXTENDABLE BONE FIXATION MEMBERS

(75) Inventors: Philipp Brun, Basel (CH); Salman Chegini, Oberdorf (CH); Philippe Lindenmann, Oberdorf (CH)

(73) Assignee: DePuy Synthes Product, LLC, Raynham, MA (US)

( * ) Notice: Subject to any disclaimer, the term of this patent is extended or adjusted under 35 U.S.C. 154(b) by 252 days.

(21) Appl. No.: 13/019,466

(22) Filed: Feb. 2, 2011

(65) Prior Publication Data
US 2012/0197404 A1 Aug. 2, 2012

(51) Int. Cl.
*A61F 2/44* (2006.01)
(52) U.S. Cl.
USPC .......................................... 623/17.11; 606/99
(58) Field of Classification Search
USPC ............ 623/17.11–17.16; 606/86 A, 99–100
See application file for complete search history.

(56) References Cited

U.S. PATENT DOCUMENTS

| | | | |
|---|---|---|---|
| 3,791,380 A | 2/1974 | Dawidowski | |
| 3,875,595 A | 4/1975 | Froning | |
| 4,599,086 A | 7/1986 | Doty | |
| 5,658,335 A | 8/1997 | Allen | |
| 5,683,394 A | 11/1997 | Rinner | |
| 5,800,547 A | 9/1998 | Schafer et al. | |
| 5,800,550 A | 9/1998 | Sertich | |
| 5,810,820 A | 9/1998 | Santori et al. | |
| 5,849,004 A | 12/1998 | Barmlet | |
| 5,888,228 A | 3/1999 | Knothe et al. | |
| 6,113,638 A | 9/2000 | Williams et al. | |
| 6,179,873 B1 | 1/2001 | Zientek | |
| 6,210,442 B1 | 4/2001 | Wing et al. | |
| 6,371,987 B1 | 4/2002 | Weiland et al. | |
| 6,447,546 B1 | 9/2002 | Bramlet et al. | |
| 6,527,803 B1 | 3/2003 | Crozet et al. | |
| 6,767,367 B1 | 7/2004 | Michelson | |
| 6,770,096 B2 | 8/2004 | Bolger et al. | |
| 6,800,092 B1 | 10/2004 | Williams et al. | |
| 6,923,830 B2 | 8/2005 | Michelson | |
| 6,981,975 B2 | 1/2006 | Michelson | |
| 7,051,610 B2 * | 5/2006 | Stoianovici et al. ............ 74/425 |

(Continued)

FOREIGN PATENT DOCUMENTS

| | | |
|---|---|---|
| DE | 4327054 | 4/1995 |
| WO | WO 99/66867 | 12/1999 |
| WO | WO 2004/080356 | 9/2004 |

OTHER PUBLICATIONS

Synthes, "Synthes Global Interent: SynFix-LR", http://www.synthes.com/html/SynFix-LR.6902.0.html, © 2009, accessed Sep. 16, 2009, 1page.

*Primary Examiner* — Todd Manahan
*Assistant Examiner* — Eric S Gibson
(74) *Attorney, Agent, or Firm* — Woodcock Washburn LLP

(57) ABSTRACT

An intervertebral implant is configured to be fixed in an intervertebral space defined by a first vertebral body and a second vertebral body. The intervertebral implant includes an implant body sized to be inserted into an intervertebral space, and a fixation assembly carried by the implant body. The fixation assembly includes a fixation housing and a plurality of fixation members attached to the fixation housing. The fixation assembly can be iterated from a retracted position to an extended position that causes the fixation members to travel along a channel of the implant body and out the implant body so as to attach the implant to the first and second vertebral bodies.

30 Claims, 14 Drawing Sheets

(56) References Cited

U.S. PATENT DOCUMENTS

| | | |
|---|---|---|
| 7,112,206 B2 | 9/2006 | Michelson |
| 7,223,289 B2 | 5/2007 | Trieu et al. |
| 7,303,583 B1 | 12/2007 | Schar et al. |
| 7,473,276 B2 | 1/2009 | Aebi et al. |
| 7,563,284 B2 | 7/2009 | Coppes et al. |
| 7,563,286 B2 | 7/2009 | Gerber et al. |
| 7,594,932 B2 | 9/2009 | Aferzon et al. |
| 7,846,188 B2 * | 12/2010 | Moskowitz et al. ........... 606/279 |
| 8,257,443 B2 * | 9/2012 | Kamran et al. ............ 623/17.16 |
| 8,303,663 B2 * | 11/2012 | Jimenez et al. ............ 623/17.16 |
| 8,313,528 B1 | 11/2012 | Wensel |
| 8,323,345 B2 * | 12/2012 | Sledge ...................... 623/17.16 |
| 2003/0187436 A1 | 10/2003 | Bolger et al. |
| 2004/0010312 A1 | 1/2004 | Enayati |
| 2005/0027362 A1 | 2/2005 | Williams et al. |
| 2005/0049590 A1 | 3/2005 | Alleyne et al. |
| 2005/0143825 A1 | 6/2005 | Enayati |
| 2005/0283236 A1 | 12/2005 | Razian et al. |
| 2006/0095136 A1 | 5/2006 | McLuen |
| 2006/0241621 A1 | 10/2006 | Moskowitz et al. |
| 2007/0049943 A1 * | 3/2007 | Moskowitz et al. ............ 606/72 |
| 2007/0179623 A1 | 8/2007 | Trieu et al. |
| 2007/0208345 A1 * | 9/2007 | Marnay et al. .................. 606/61 |
| 2007/0270960 A1 * | 11/2007 | Bonin et al. ................ 623/17.11 |
| 2007/0270961 A1 | 11/2007 | Ferguson |
| 2008/0132949 A1 | 6/2008 | Aferzon et al. |
| 2008/0177306 A1 | 7/2008 | Lamborne et al. |
| 2009/0099601 A1 | 4/2009 | Aferzon et al. |
| 2009/0112271 A1 | 4/2009 | Moskowitz et al. |
| 2009/0164020 A1 | 6/2009 | Janowski et al. |
| 2009/0265007 A1 | 10/2009 | Colleran |
| 2010/0016974 A1 * | 1/2010 | Janowski et al. .......... 623/17.16 |
| 2010/0161057 A1 * | 6/2010 | Berry et al. ................ 623/17.16 |
| 2010/0185289 A1 * | 7/2010 | Kirwan et al. ............. 623/17.11 |
| 2010/0298941 A1 * | 11/2010 | Hes et al. ................... 623/17.16 |
| 2011/0112587 A1 * | 5/2011 | Patel et al. .................. 606/86 A |
| 2011/0178599 A1 * | 7/2011 | Brett ......................... 623/17.16 |
| 2011/0208311 A1 * | 8/2011 | Janowski .................... 623/17.16 |
| 2012/0022654 A1 * | 1/2012 | Farris et al. ................ 623/17.16 |
| 2012/0197404 A1 * | 8/2012 | Brun et al. ................. 623/17.16 |

\* cited by examiner

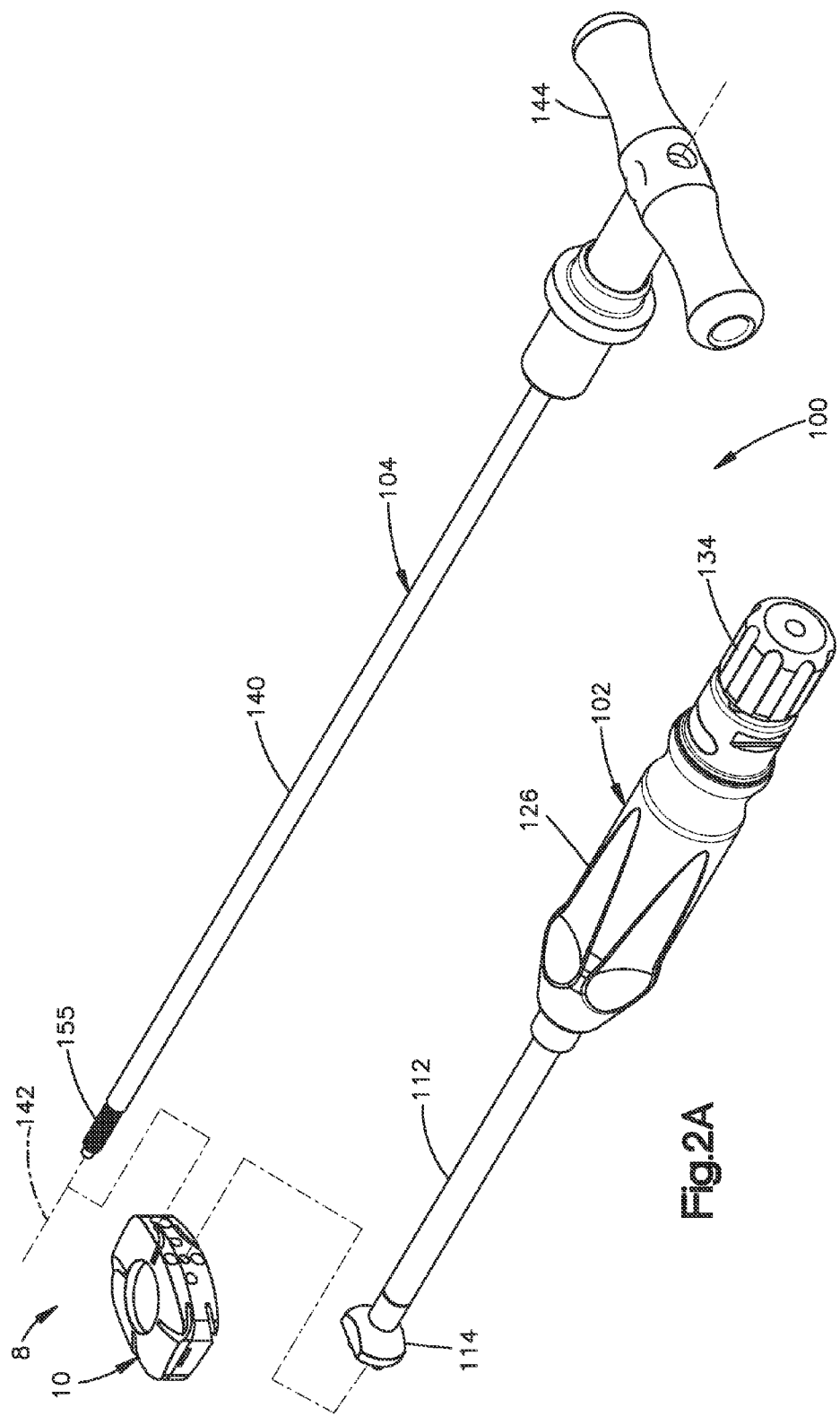

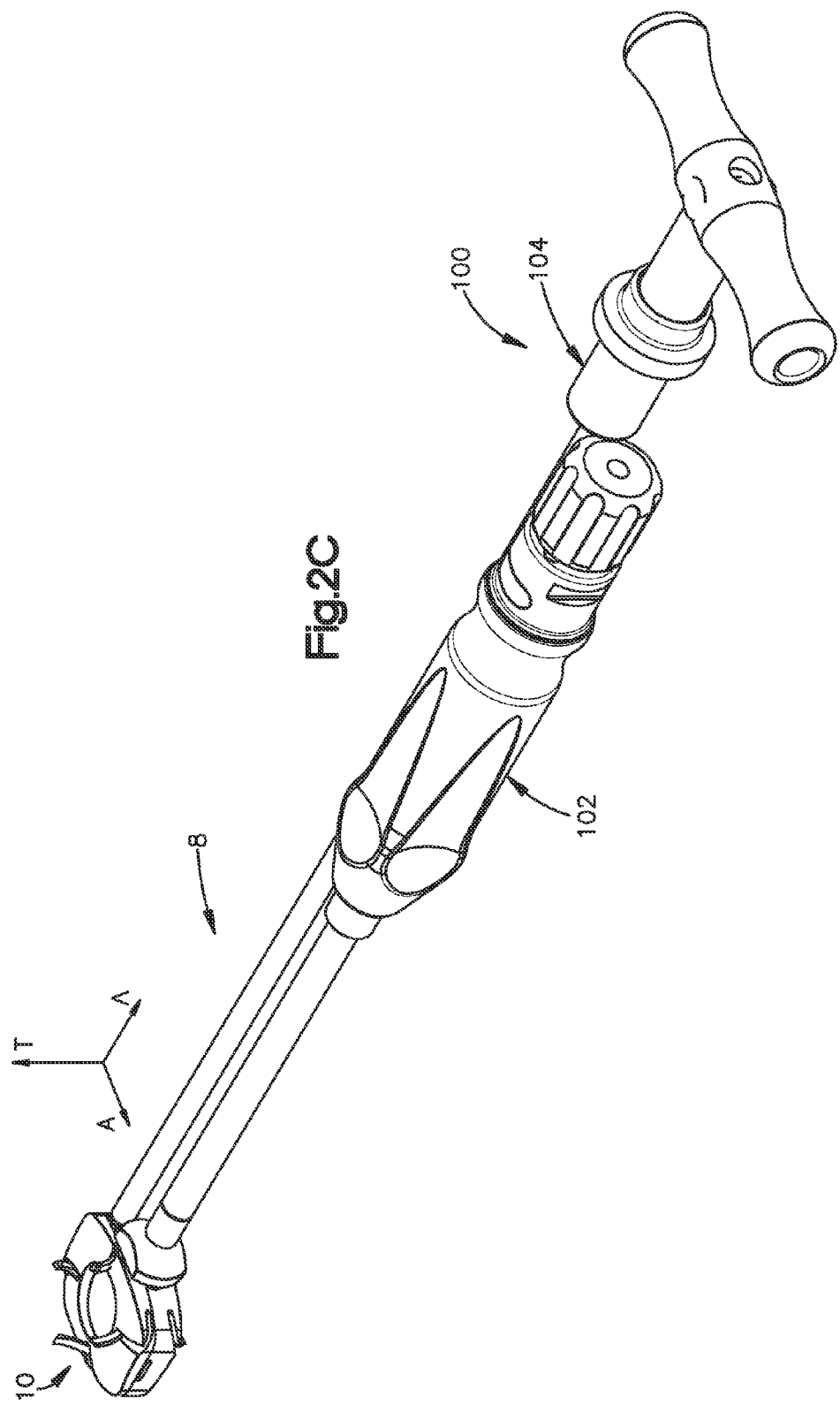

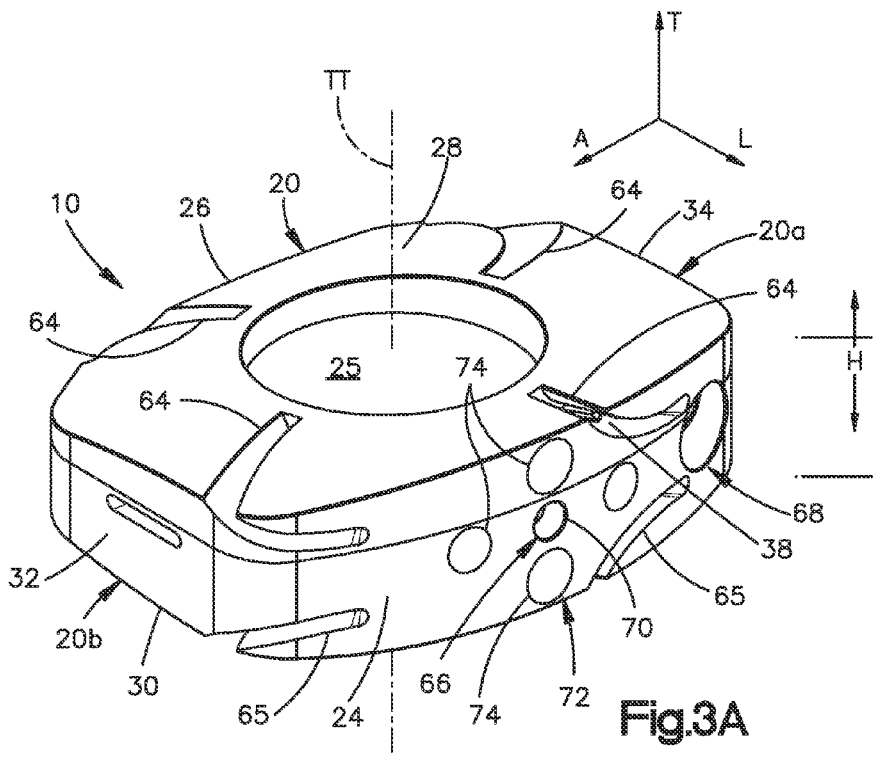
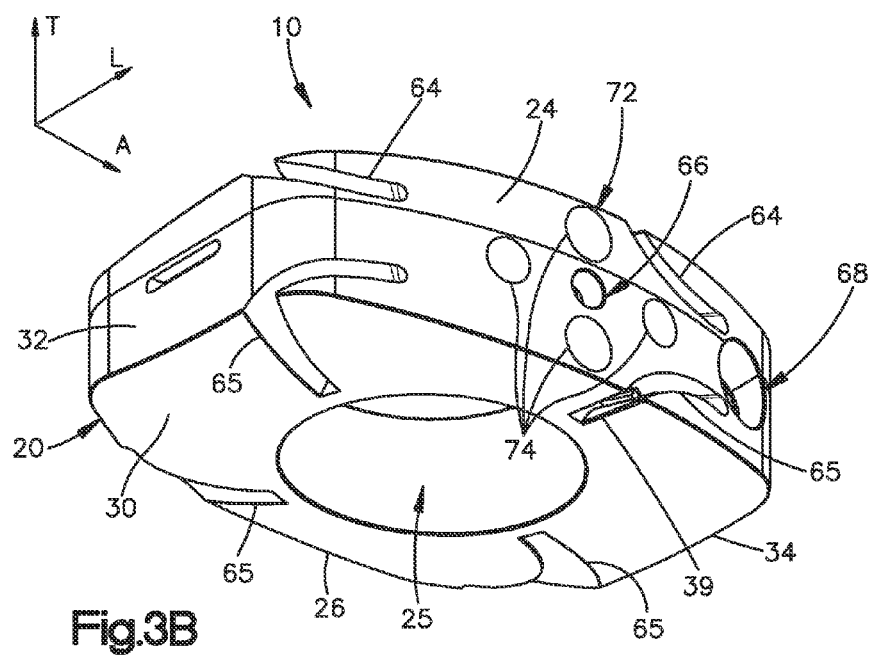

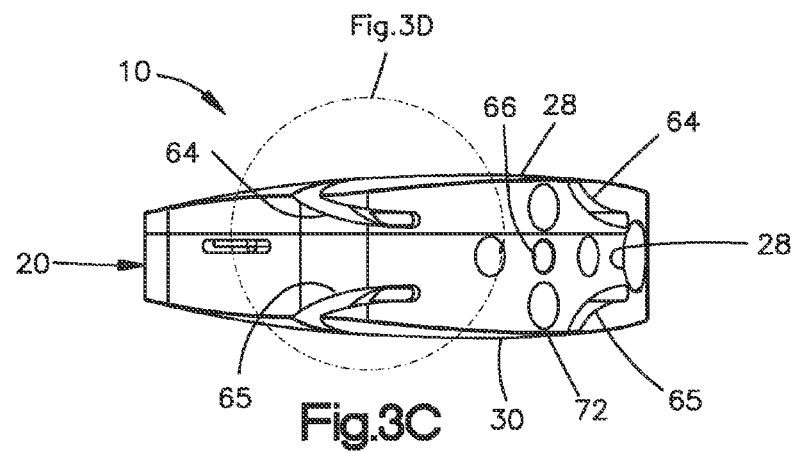
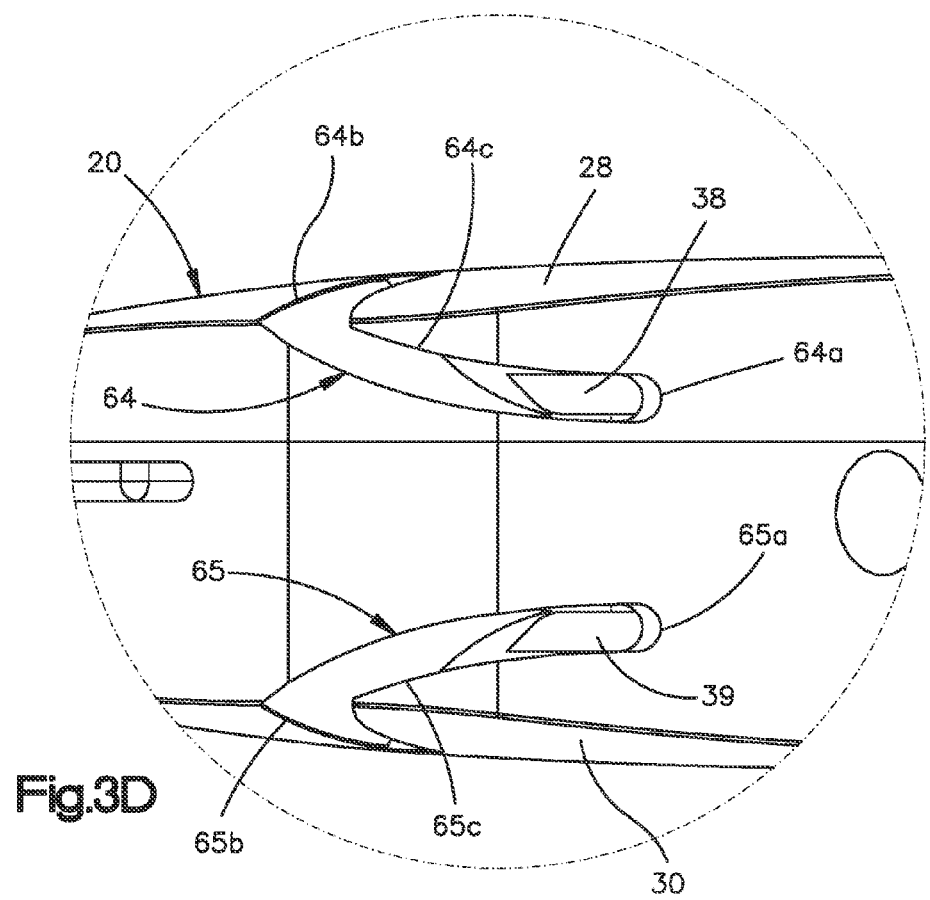

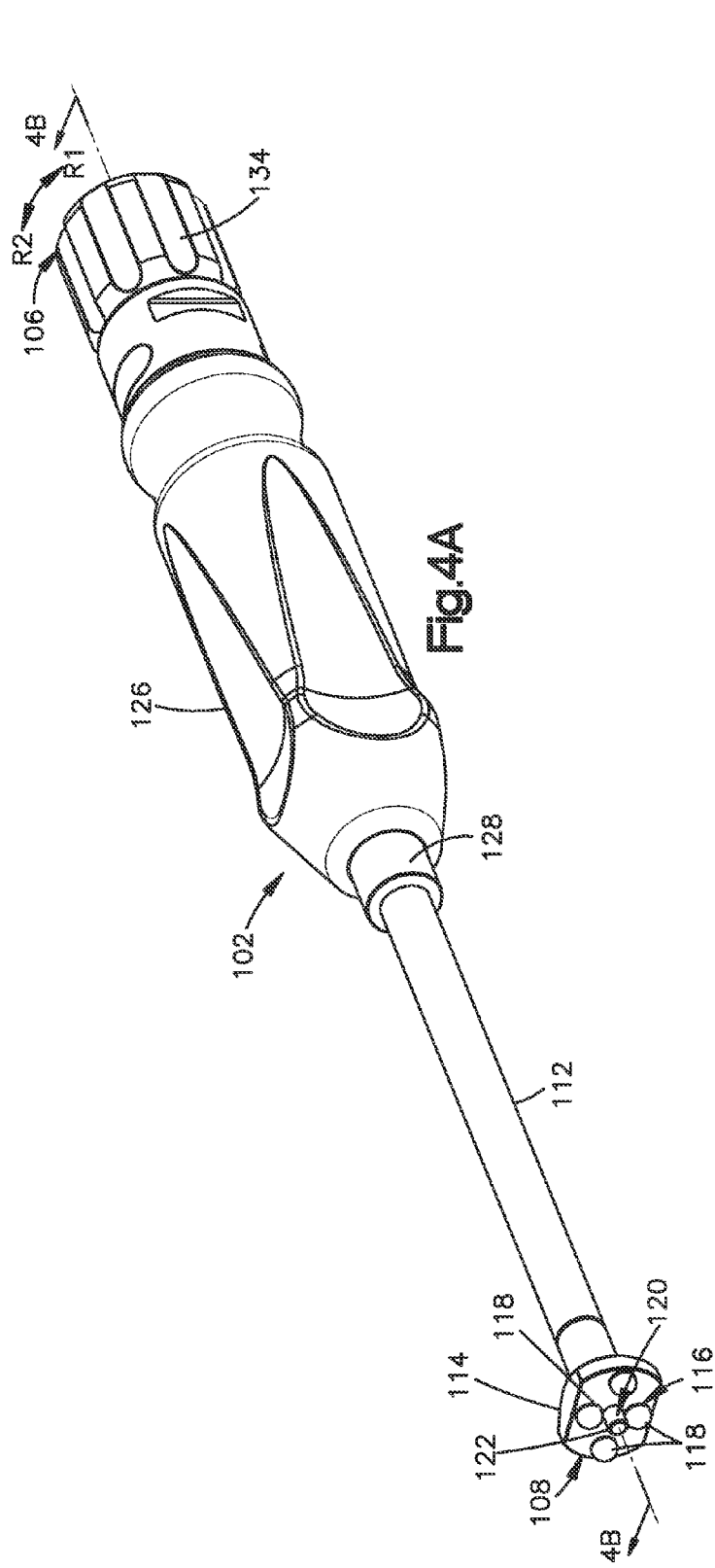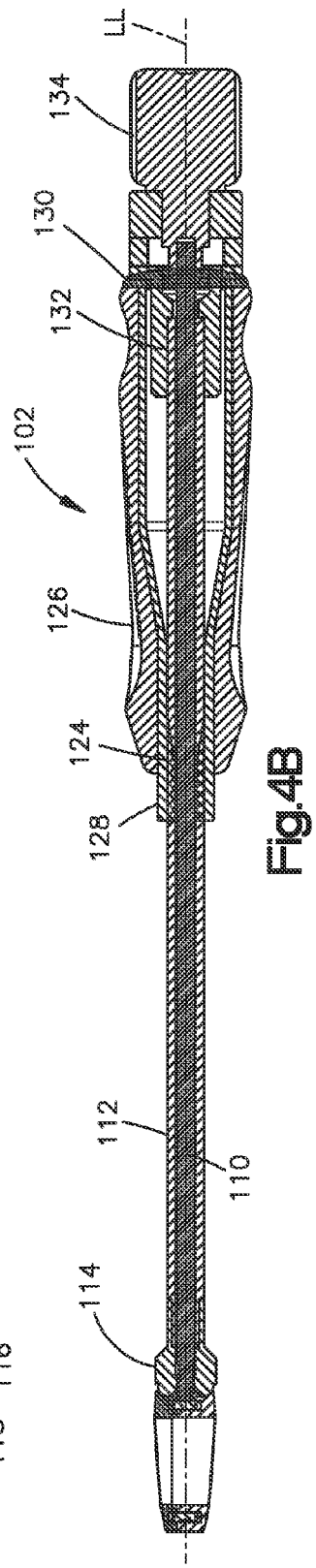

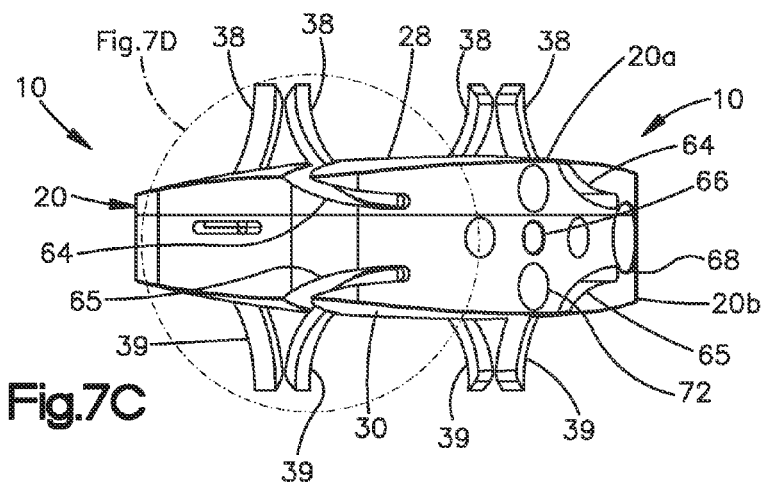
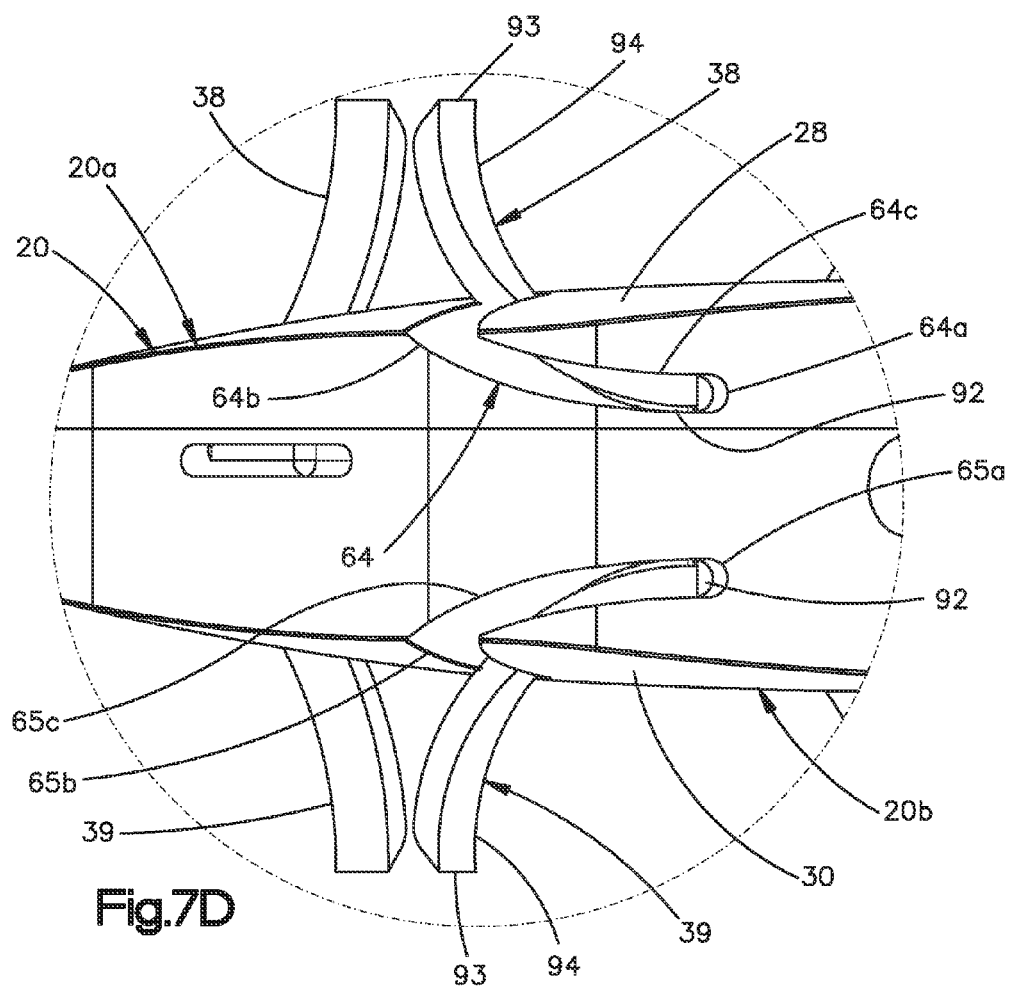

INTERVERTEBRAL IMPLANT HAVING EXTENDABLE BONE FIXATION MEMBERS

CROSS-REFERENCE TO RELATED APPLICATIONS

This is related by subject matter to U.S. patent application Ser. No. 12/884,664, filed on Sep. 17, 2010, the disclosure of which is hereby incorporated by reference as if set forth in its entirety herein.

BACKGROUND

The human vertebral column (also known as the backbone or spine) houses the spinal cord in its spinal canal. The vertebral column is made up of a plurality of vertebrae. A typical vertebra includes two primary parts, including an anterior portion that includes the vertebral body, and a posterior portion that encloses the foramen. Each vertebral body defines superior and inferior vertebral endplates that, such that adjacent vertebrae define an intervertebral space that includes disc material between the respective endplates.

Historically, spinal abnormalities have indicated complete removal of a disc from the intervertebral space followed by fusion the adjacent vertebrae together. This "spinal fusion" procedure, which is still in use today, is a widely accepted surgical treatment for symptomatic lumbar and cervical degenerative disc disease. Early fusion procedures used an implant made of bone from a patient's hip or a cadaver bone as a spacer in the intervertebral space so as to properly position the adjacent vertebrae until the vertebrae were fused together. More modern procedures use implants made from a material having a relatively low modulus of elasticity to encourage bone growth. For instance, the implant can contain some of the patient's own bone, e.g., within apertures of the implant. Conventional implants can be made from desired material, including radiolucent materials such as polyetheretherketone (PEEK), ultra-high molecular weight polyethylenes (UHMWPE) or polysulfones (PSU).

Conventional intervertebral implant designs have attempted to achieve implant fixation in the intervertebral space.

SUMMARY

In accordance with one embodiment, an intervertebral implant is configured to be fixed in an intervertebral space defined by a first vertebral body and a second vertebral body. The intervertebral implant includes an implant body sized to be inserted into an intervertebral space. The implant body defines superior and inferior vertebral facing surfaces that are spaced along a transverse direction. The implant body further defines a superior channel that is open at the superior vertebral facing surface, and an inferior channel that is open at the inferior vertebral facing surface. The intervertebral implant further includes a fixation assembly carried by the implant body. The fixation assembly includes a fixation housing extending along a substantially transverse axis, a superior vertebral fixation member carried by the housing and configured to travel in the superior channel, and an inferior vertebral fixation member carried by the housing and configured to travel in the inferior channel. The fixation assembly is rotatable within the implant body about the substantially transverse axis from a retracted position to an extended position whereby the superior and inferior vertebral fixation members travel in the superior and inferior channels, respectively, so as to extend out from the superior and inferior surfaces, respectively.

BRIEF DESCRIPTION OF THE DRAWINGS

The foregoing summary, as well as the following detailed description of example embodiments of the present disclosure, will be better understood when read in conjunction with the appended drawings. For the purposes of illustrating the example embodiments of the present disclosure, references to the drawings are made. It should be understood, however, that the application is not limited to the precise arrangements and instrumentalities shown. In the drawings:

FIG. 2A is an exploded assembly view of the implant assembly including an intervertebral implant and an instrument assembly including an insertion tool configured to insert the implant in an intervertebral space and an actuation tool configured to iterate the implant from a first retracted position to a second extended position;

FIG. 2C is a top perspective view of the implant assembly illustrated in FIG. 2A, showing the instrument assembly attached to the intervertebral implant, and showing the intervertebral implant in the second extended position;

FIG. 3A is a top perspective view of the intervertebral implant illustrated in FIG. 2A, shown in a first retracted position;

FIG. 3B is a bottom perspective view of the intervertebral implant illustrated in FIG. 3A;

FIG. 3C is a side elevation view of the intervertebral implant illustrated in FIG. 3A;

FIG. 3D is an enlarged side elevation view of the intervertebral implant illustrated in FIG. 3C, taken at region 3D;

FIG. 4A is a perspective view of the insertion tool illustrated in FIG. 2A;

FIG. 4B is a sectional side elevation view of the insertion tool illustrated in FIG. 4A, taken along line 4B-4B and shown attached to the intervertebral implant;

FIG. 7C is a side elevation view of the intervertebral implant illustrated in FIG. 7A; and FIG. 7D is an enlarged side elevation view of the intervertebral implant illustrated in FIG. 7C, taken at region 7D.

DETAILED DESCRIPTION

Figure 1A:
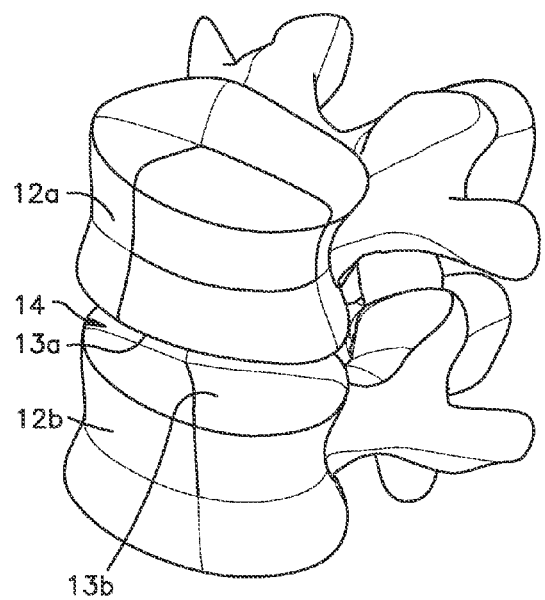
FIG. 1A is a perspective view of a pair of vertebral bodies separated by an intervertebral space.
Figure 1B:
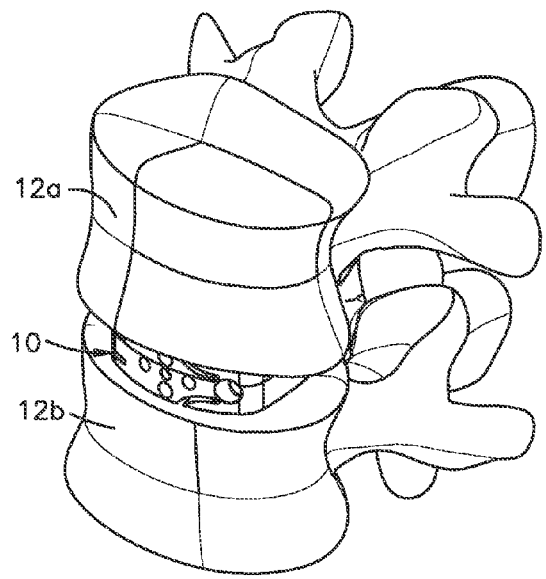
FIG. 1B is a perspective view of the vertebral bodies illustrated in FIG. 1, and an intervertebral implant inserted into and fixed in the intervertebral space between the two vertebral bodies illustrated in FIG. 1A.

Referring to FIGS. 1A-B, a first superior vertebral body 12a defines a superior vertebral endplate 13a of an intervertebral space 14, and an adjacent second inferior vertebral body 12b defines an inferior vertebral endplate 13b of the intervertebral space 14. Thus, the intervertebral space 14 is disposed between the vertebral bodies 12a-b. The vertebral bodies 12a-b can be anatomically adjacent vertebral bodies, or can remain after a discectomy has been performed that removed a vertebral body from a location between the vertebral bodies 12a-b. As illustrated, the intervertebral space 14 is illustrated after a discectomy, whereby the disc material has been removed to prepare the intervertebral space 14 to receive an orthopedic implant, such as the intervertebral implant 10 illustrated in FIG. 2A. Thus, the implant 10 is configured to be inserted into the intervertebral space 14, and achieve restoration of height and help fusion of the segment. The intervertebral space 14 can be disposed anywhere along the spine as desired. As will be appreciated from the description below, the implant 10 can be sized as desired so as to be implantable in an intervertebral disc space in any region of the spine, including the lumbar region, thoracic region, cervical region, sacral region, and coccygeal region.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior," "superior," "inferior," "medial," "lateral," and related words and/or phrases designate preferred positions and orientations in the human body to which reference is made and are not meant to be limiting. The terminology includes the above-listed words, derivatives thereof and words of similar import.

The implant 10 and various components of the implant 10 are described herein extending horizontally along a longitudinal direction L and a lateral direction A, and vertically along a transverse direction T. Unless otherwise specified herein, the terms "lateral," "longitudinal," and "transverse" are used to describe the orthogonal directional components of various components. The lateral direction A and longitudinal direction L are angularly offset, for instance substantially orthogonal, with respect to each other and with respect to the transverse direction T. It should be appreciated that while the longitudinal and lateral directions are illustrated as extending along a horizontal plane, and that the transverse direction is illustrated as extending along a vertical plane, the planes that encompass the various directions may differ during use. For instance, when the implant 10 is implanted into an intervertebral space, such as the intervertebral space 14, the transverse direction T extends generally along the superior-inferior (or cranial-caudal) direction, while the plane defined by the longitudinal direction L and lateral direction A lie generally in the anatomical plane defined by the anterior-posterior direction, and the medial-lateral direction, respectively. Accordingly, the directional terms "vertical" and "horizontal" are used to describe the implant 10 and its components as illustrated merely for the purposes of clarity and illustration.

Figure 2B:
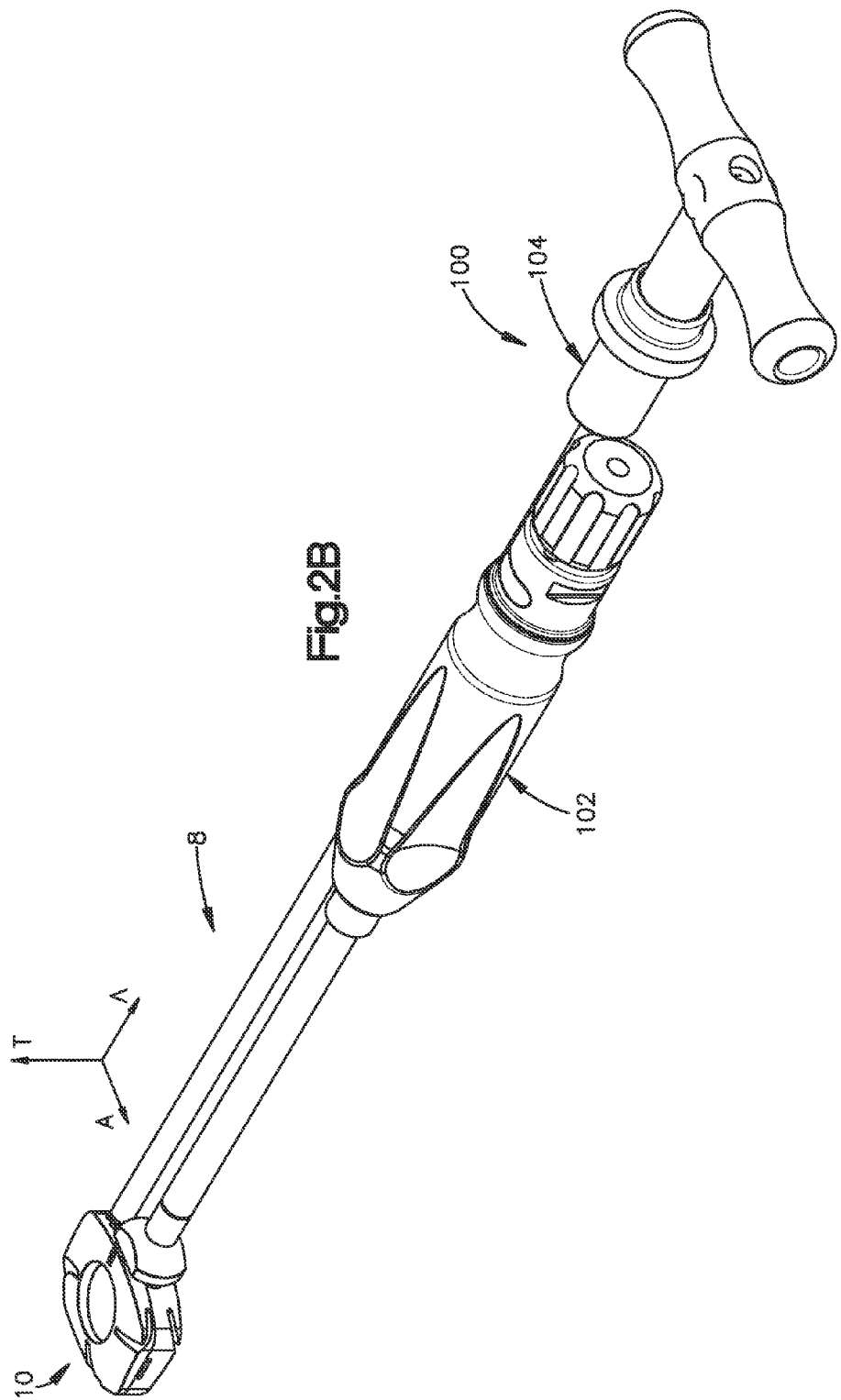
FIG. 2B is a top perspective view of the implant assembly illustrated in FIG. 2A, showing the instrument assembly attached to the intervertebral implant, and showing the intervertebral implant in the first retracted position.

Referring to FIGS. 2A-C, an intervertebral implant assembly 8 includes the intervertebral implant 10 along with an instrument assembly 100 that is configured to insert the intervertebral implant 10 in the intervertebral space 14 and actuate the implant 10 from a first retracted position (FIG. 2B) to a second extended position (FIG. 2C). The instrumentation assembly 100 includes an insertion tool 102 that is configured to grip the body 20 of the implant 10, and an actuation tool 104 that is configured to iterate the implant 10 from the first retracted position to the second extended position. The insertion tool 102 can be separate and discrete with respect to the actuation tool 104 such that the insertion tool 102 and the actuation tool 104 can be independently attached to, and removed from, the implant 10. Alternatively, the insertion tool 102 and the actuation tool 104 can be integral with each other, and thus can be attached to, and removed from, the implant 10 in unison.

The implant 10, instrumentation assembly 100, and components thereof can be formed from any of any suitable material, such as a variety of biocompatible materials, including but not limited to cobalt chromium molybdenum (CoCrMo), titanium and titanium alloys, stainless steel, ceramics, or polymers such as polyetheretherketone (PEEK), ultra-high molecular weight polyethylenes (UHMWPE) or polysulfones (PSU), bioresorbable materials, and bonegraft (for example allograft and xenograft). A coating may be added or applied to the implant body 20 to improve physical or chemical properties. The coatings may help to ensure bony in or on growth or medication. Examples of coatings include plasma-sprayed titanium coating or hydroxyapatite.

Referring also to FIGS. 3A-D, the implant body 20 extends along a substantially central trasverse axis TT, and defines a front end 24 and a longitudinally opposed rear end 26, a top end 28 and a transversely opposed bottom end 30, and laterally opposed sides 32 and 34. The top and bottom ends 28 and 30 can be configured to face the corresponding vertebral endplates 13a and 13b of the superior and inferior vertebral bodies 12a and 12b, respectively. Thus, the top end 28 can define a first vertebral facing surface that is configured to face the vertebral endplate 13a, and the bottom end, and the bottom end 30 can define a second vertebral facing surface that is configured to face the vertebral endplate 13b when the implant is disposed in the intervertebral space 14. In some embodiments, the top and bottom ends 28 and 30 can be configured to abut the corresponding vertebral endplates 13a and 13b (see FIG. 1B). The implant 10 can be inserted into the intervertebral space 14 along an insertion direction which can be an anterior-posterior approach (for instance when the vertebral bodies 12a and 12b are cervical vertebral bodies) in an orientation such that the front longitudinal end 24 is anterior to the rear longitudinal end 26. By modification of the size and shape of the implant, the implant can be inserted from lateral antero-lateral or poster-lateral side of the segment into the disc space.

The implant body 20 can be sized and shaped as desired, and is illustrated as substantially rectangular that can have curved outer surfaces. For instance, the front end 24 can extend substantially laterally and can be curved or otherwise angled longitudinally outward along a laterally outward direction of travel its midpoint. Likewise, the rear end 26 can extend substantially laterally and can be curved or otherwise angled longitudinally inward along a laterally outward direction of travel from its midpoint. Similarly, the lateral sides 32 and 34 can extend subsantially longitudinally and can be curved or otherwise angled laterally inward toward each other along a longitudinally outward direction of travel from their respective midpoints. In accordance with the illustrated embodiment, the implant 10 defines a substantially central opening 25 that extends transversely into (through as illustrated) the implant body 20. The central opening 25 can be any size and shape as desired, such as cylindrical as illustrated, and configured to receive any suitable bone growth promoting material, such as allograft and xenograft to promote bone growth with the vertebral bodies 12a-b after implantation of the implant 10 into the intervertebral space 14. The implant body 20 can be solid as illustrated, or can define perforations that extend into or through the implant body 20 that can, for instance, receive the bone growth promoting material. The implant 10 can further include a plurality of teeth or spikes that extend transversely out from the upper and lower ends 28 and 30 as desired so as to enhance fixation of the implant body 20 to the vertebral bodies 12a-b, respectively.

The implant body 20 defines a transverse height H between the top and bottom ends 28 and 30. The height H can be substantially constant from the front end 24 to the rear end 26, or can be variable from the front end 24 to the rear end 26 so as to impart or restore a lordotic curvature to the vertebral bodies 12a and 12b. Thus, the height H can decrease in a rearward direction from the front end 24 toward the rear end 26, or can increase in the rearward direction. Furthermore, the height H can be constant or variable between the lateral sides 32 and 34 as desired. In this regard the top and bottom ends 28 and 30 can be substantially planar, or can be curved, undulated, or otherwise shaped as desired so as to correspond to the vertebral endplates 13a and 13b. A kit of implants 10 can also be provided, each having a plurality of implant bodies 20 of different shapes or sizes. For instance, the kit can include a plurality of implant bodies 20 of different heights H, such that at least one of the implant bodies 20 in the kit can correspond with the corresponding different height of intervertebral spaces along the vertebral column of a given patient, or of an intervertebral space of different patients.

With continuing reference to FIGS. 2A-3D, the implant 10 defines at least one channel such as a plurality of upper, or superior, channels 64 and lower, or inferior, channels 65 that extend into the implant body 20, and a like number of fixation members such as a plurlaity of upper, or superior, vertebral fixation members 38 and lower, or inferior, vertebral fixation members 39 that are configured to ride along the respective channels 64 and 65 from the first retracted position to the second extended position. When the implant 10 is in the first retracted position, the vertebral fixation members 38 and 39 do not extend transversely out from the implant body 20 through the channels 64 and 65, and are thus recessed with respect to the top and bottom ends 28 and 30, respectively. Alternatively, the fixation members 38 and 39 can extend slightly transversely out from the top and bottom ends 28 and 30, respectively, of the implant body 20 through the channels 64 and 65. When the implant 10 is in the second extended position, the vertebral fixation members 38 and 39 extend out from the implant body 20 through the channels 64 and 65 a distance suitable to be inserted into the adjacent vertebral endplates 13a and 13b, respectively, so as to fix the implant to the vertebrae 12a and 12b in the intervertebral space 14. Thus, whether the fixation members 38 and 39 extend slightly out the implant body 20 or are recessed in the implant body 20 when the implant 10 is in the retracted position, it can be said that the fixation members 38 and 39 extend out from the implant body 20, such as the top and bottom ends 28 and 30, respectively, a distance that is greater than when the implant 10 is in the retracted position.

The implant 10 can include any number of channels 64 and 65 as desired that are spaced substantially equidistantly about the implant body 20 as illustrated or can be variably spaced about the implant body 20 as desired. In accordance with the illustrated embodiment, the channels 64 and 65 are substantially identically constructed and symmetrical, though it should be appreciated that the channels 64 and 65 can alternatively have different sizes and shapes suitable to guide the fixation members 38 and 39 out the implant body 20 and into the adjacent vertebral bodies 12a and 12b. Furthermore, in accordance with the illustrated embodiment, the upper channels 64 can be at least partially aligned, for instance substantially aligned, with the lower channels 65 with respect to the transverse direction, such that transverse extending lines that pass through the upper channels 64 likewise pass through the lower channels 65.

Each channel 64 and 65 can include respective inner transverse leading ends 64a and 65a that terminate in the implant body 20, outer transverse trailing ends 64b and 65b that are open to the top and bottom ends 28 and 30, respectively, and intermediate regions 64c and 65c that extend from the leading ends 64a and 65a to the trailing ends 64b and 65b. In accordance with the illustrated embodiment, the intermediate regions 64c and 65c, and thus the channels 64 and 65, define a curvilinear path from the respective leading ends 64a and 65a to the trailing ends 64b and 65b, though it should be appreciated that the channels 64 and 65 can define any suitably sized and shaped path as desired. In accordance with the illustrated embodiment, the trailing ends 64b and 65b are offset with respect to the leading ends 64a and 65a with respect to a rotational direction, such as a clockwise direction, about the central transverse axis. For instance, the leading ends 64a and 65a extend substantially horizontally, and the trailing ends 64b and 65b extend substantially transversely outward. For instance, the upper trailing ends 64b extend substantially upward and the lower trailing ends 65b extend substantially downward.

Referring now to FIGS. 3A-3B in particular, the implant 10 defines a first attachment location 66 and a second attachment location 68 that are configured to attach to the insertion tool 102 and the actuation tool 104, respectively. The first attachment location 66 is illustrated as an aperture 70 that extends longitudinally rearward into the front end 24 of the implant body 20. The implant 10 can further define at least one brace location 72 such as a plurality of brace locations 72 illustrated as depressions 74 that extend into the implant body, such as at the front end 24, at a location adjacent the first attachment location 66. In accordance with the illustrated embodiment, the depressions 74 are disposed substantially symmetrically and equidisantly about the first attachment location 66. Furthermore, while the implant 10 includes four depressions 74 in accordance with the illustrated embodiment, the implant 10 can include as many depressions as desired. It should be further appreciated that while the brace locations 72 are illustrated as depressions, the brace locations 72 can be configured as desired, and for instance can be provided as projections that extend from, for example, the front end 24 of the implant body 20.

Figure 4C:
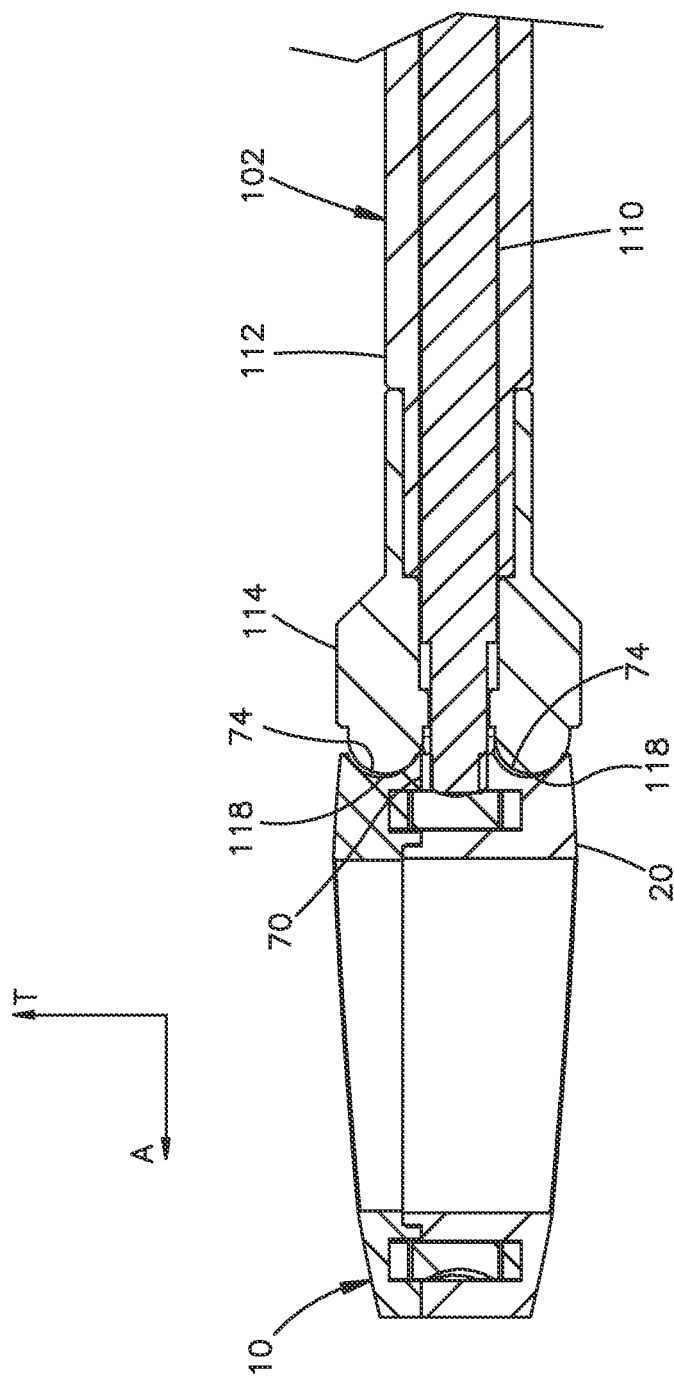
FIG. 4C is an enlarged sectional side elevation view of a distal portion of the insertion tool shown attached to the intervertebral implant as illustrated in FIG. 4B.

Referring now to FIGS. 4A-C, the insertion tool 102 extends along a substantially central longitudinal axis LL, and defines a proximal end 106 and a distal end 108 that is opposite the proximal end 106 along the longitudinal axis LL. The insertion tool 102 includes a sleeve 112 and a translatable member such as a shaft 110 that is disposed inside the sleeve 112. The insertion tool 102 further defines a support member such as a support plate 114 that extends outward from the distal end of the sleeve 112, and a plurality of brace members 116 that are illustrated as projections 118 that extend distally from the support plate 114. The brace members 116 are configured to abut the front end 24 of the implant body 20, for instance at the brace locations 72 such that the projections 118 are received in the depressions 74 so as to stabilize the insertion tool 102 when the insertion tool is attached to the implant 20. The insertion tool 102 further includes an engagement member 120 in the form of a projection 122 that extends distally through the support plate 114 and extends distally with respect to the support plate 114. The projection 122 can be any size and shape, and can be sized slightly less than or substantially equal to the aperture 70 so as to be press-fit inside the aperture 70 to thereby attach the engagement member 120 of the insertion tool 102 to the implant 10 at the attachment location 66. The projection 122 can be inserted into the aperture 70 to a depth such that the brace members 116 abut the front end 24 of the implant body 20, or can be inserted to a depth such that the brace members 116 are spaced proximally with respect to the front end 24 of the implant body 20.

In accordance with the illustrated embodiment, the projections 118 are disposed substantially symmetrically and equidisantly about the projection 122. Furthermore, while the insertion tool 102 includes projections 118 in accordance with the illustrated embodiment, the implant 10 can include as many projections 118 as desired. It should be further appreciated that while the brace members 116 are illustrated as projections, the brace members 116 can be configured as desired, and for instance can be provided as depressions that extend into the support plate 114.

The shaft 110 is threadedly mated to the sleeve 112 at a junction 124, such that rotation of the shaft 110 in a first rotational direction R1 causes the shaft 110 to translate proximally along the longitudinal axis LL with respect to the sleeve 112, and rotation of the shaft 110 in a second rotational direction R2 opposite the first rotational direction causes the shaft 110 to translate distally along the longitudinal axis LL with respect to the sleeve. It should be appreciated that as the shaft 110 translates distally with respect to the sleeve 112, the projection 122 likewise translates distally with respect to the support plate 114 and thus the brace members 116. As the shaft 110 translates proximally with respect to the sleeve 112, the projection 122 likewise translates proximally with respect to the support plate 114 and thus the brace members 116.

The insertion tool 102 further includes a collar 128 that is attached at its distal end to the sleeve 112, and a handle 126 that is mounted to the collar 128 and thus supported by the shaft 110 and sleeve 112. The handle 126 defines an end plate 130 at its proximal end and supports a bearing 132 that is disposed adjacent the end plate 130, for instance at a location distal of the end plate 130. The bearing 132 is fixedly attached to the proximal end of the sleeve 112, and further supports the shaft 110 so as to allow the shaft 110 to rotate relative to the handle 126. The insertion tool 102 further includes an actuator, such as a rotatable knob 134, that is rotatably supported by the handles 126 at the proximal end of the insertion tool 102. The shaft extends through the bearing 132 and is fixedly attached to the knob 134, such that rotation of the knob 134 causes the shaft 110 to likewise rotate.

Accordingly, rotation of the knob 134 along the first rotational direction R1 causes the shaft 110 to likewise rotate in the direction R1, which causes the shaft 110 and thus the projection 122 to translate, or withdraw, proximally along the longitudinal axis LL. Likewise, rotation of the knob 134 along the second rotational direction R2 causes the shaft 110 to likewise rotate in the direction R2, which causes the shaft 110 and thus the projection 122 to translate, or extend, distally along the longitudinal axis LL. During operation, the shaft 110 is advanced distally to a position such that the projection 122 can be inserted into the aperture 70 prior to engagement of the brace members 116 with the front end 24 of the implant body 20, thereby attaching the insertion tool 102 to the implant 100. The user can then grab the handle 126 and manipulate the insertion tool 102 so as to insert the implant 10 in the intervertebral space 14 (see FIG. 1B). Once the implant 10 is positioned in the intervertebral space 14 as desired, the user can rotate the knob 134 in the rotational direction R1, which causes the shaft 110 and thus the projection 122 to translate proximally, thereby also causing the implant 10 to translate proximally with the projection 122 press-fit in the aperture 70 until the front end 24 of the implant body 20 abuts the support plate 114, which can cause the projections 118 to be seated in the complementary depressions 74. Alternatively, the projections 118 can be seated in the depressions 74 when the insertion tool 102 inserts the implant 10 into the intervertebral space. Further rotation of the knob in the rotational direction R1 causes the projection 122 to travel proximally while the implant 10 remains stationary against the brace members 116 until the projection 122 is withdrawn from the aperture 70, thereby detaching the insertion tool 102 from the implant 10.

Figure 5A:
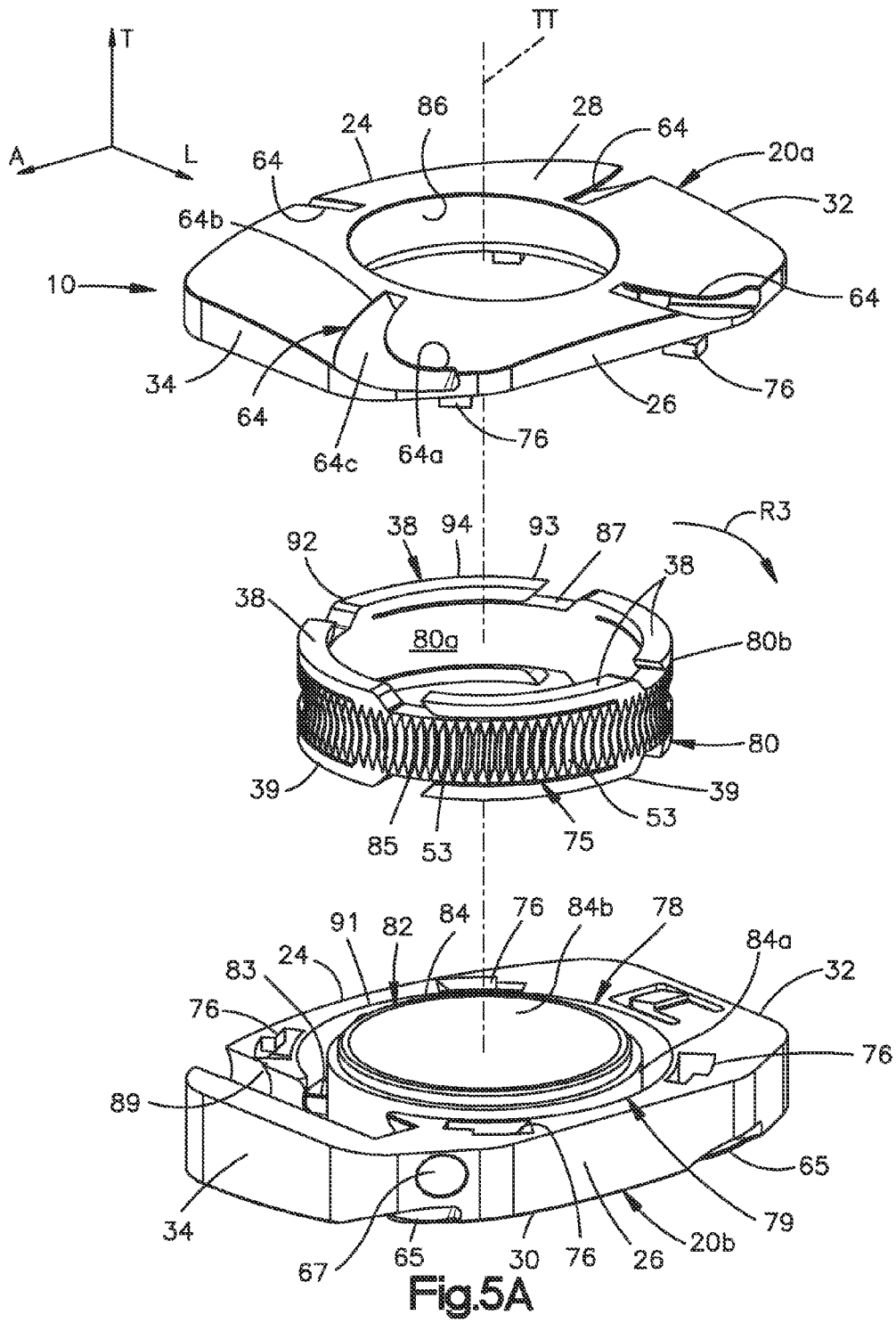
FIG. 5A is an exploded perspective view of the intervertebral implant illustrated in FIG. 3A, including an upper body portion, a lower body portion, and a fixation assembly configured to fix the implant to adjacent vertebral bodies.
Figure 5B:
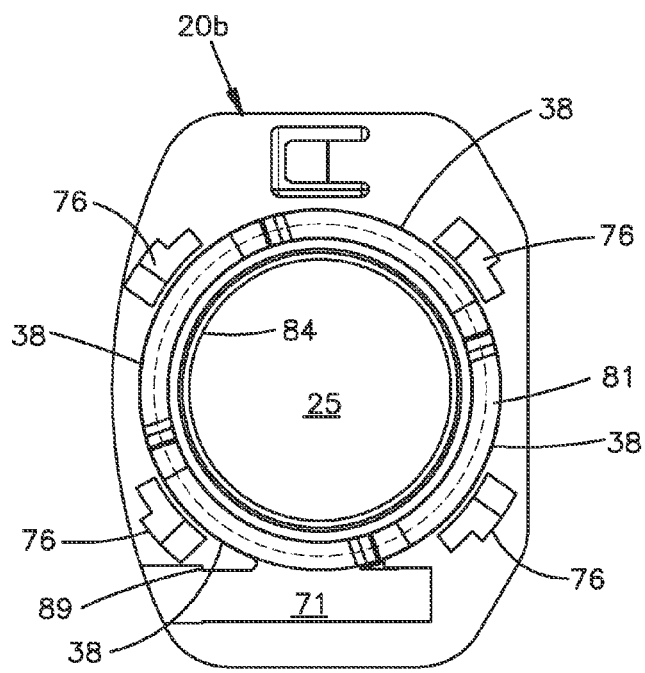
FIG. 5B is a top plan view of a portion of the intervertebral implant illustrated in FIG. 5A, showing the fixation assembly mounted to the lower body portion.
Figure 5C:
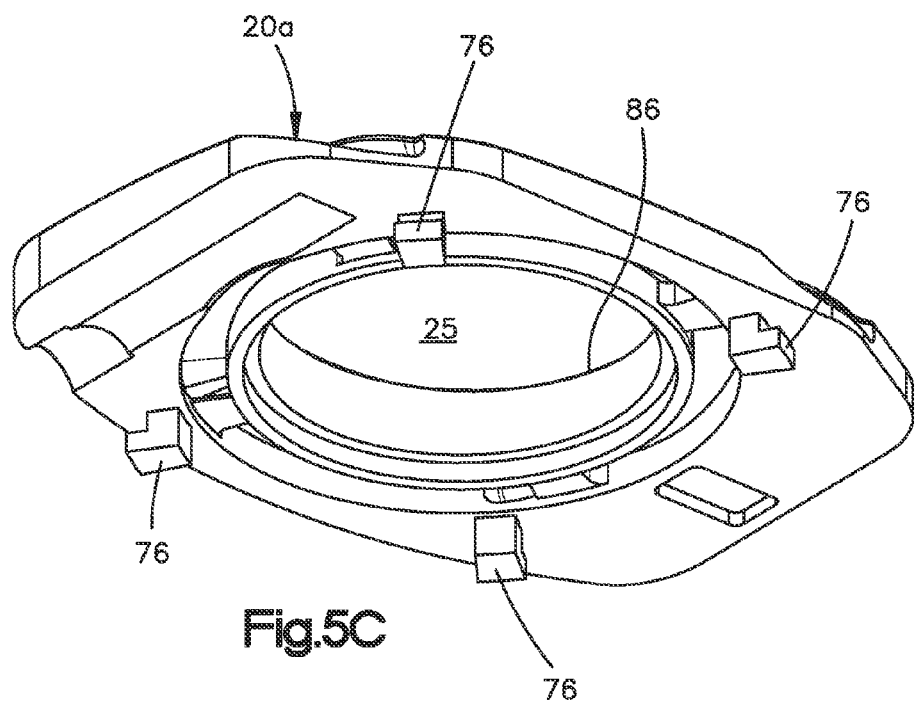
FIG. 5C is a bottom perspective view of the upper body portion illustrated in FIG. 5A.

Referring now to FIGS. 5A-5C, the implant body 20 includes an upper body portion 20a, a lower body portion 20b, and a fixation assembly 22 carried by the implant body 20 and in particular captured between the upper body portion 20a and the lower body portion 20b, and configured to fix the implant 10 to the adjacent vertebral bodies. The upper body portion 20a defines the upper channels 64 in the manner described above, and the lower body portion 20b defines the lower channels 64 in the manned described above. The upper and lower body portions 20a and 20b define complementary engagement members 76, such as tabs and slots which can be carried by either of the upper and lower body portions, respectively, that are configured to mate so as to attach the upper body portion 20a to the lower body portion 20b so as to define a recess 78 therebetween.

The fixation assembly 22 includes a fixation housing 80 and further includes the upper and lower fixation members 38 and 39 that are carried by the fixation housing 80 such that the upper fixation member 38 is disposed superior with respect to the fixation housing 80 and the lower fixation member 39 is disposed inferior with respect to the fixation housing 80. The fixation housing 80 is disposed in the recess 78 and movable within the recess 78 between the first retracted position and the second extended position. When the fixation housing 80 is in the first retracted position, the vertebral fixation members 38 and 39 do not extend transversely out from the implant body 20 through the channels 64 and 65, and are thus recessed with respect to the top and bottom ends 28 and 30, respectively. Alternatively, the fixation members 38 and 39 can extend slightly transversely out from the top and bottom ends 28 and 30, respectively, of the implant body 20 through the channels 64 and 65. When the fixation housing 80 is in the second extended position, the vertebral fixation members 38 and 39 extend out from the implant body 20 through the channels 64 and 65 a distance suitable to be inserted into the adjacent vertebral endplates 13a and 13b, respectively, so as to fix the implant to the vertebrae 12a and 12b in the intervertebral space 14. Thus, whether the fixation members 38 and 39 extend slightly out the implant body 20 or are recessed in the implant body 20 when the fixation housing 80 is in the retracted position, it can be said that the fixation members 38 and 39 extend out from the implant body 20, such as the top and bottom ends 28 and 30, respectively, a distance in the extended position that is greater than when the fixation housing 80 is in the retracted position.

In accordance with the illustrated embodiment, the lower housing portion 20b defines a central guide member 82 illustrated as a hub 84 defines an outer surface 84a and an opposed inner surface 84b. The upper housing portion 20a defines a complementary central hub 86 that can fit over or inside the central hub 84 of the lower housing portion 20b when the first and second housing portions 20a and 20b are attached. The inner surface 84b can at least partially define the central opening 25 (see FIG. 3A). The recess 78 is disposed between the outer surface 84a, and thus the hub 84, and both the front and rear ends 24 and 26 and the opposed sides 32 and 34 which combine to define an outer perimeter 91 of the recess 78. The outer surface 84a can be substantially cylindrical, such that the recess 78 can be curved. In accordance with the illustrated embodiment, the recess 78 is substantially annular, and defines an annular track 79 that defines a curvilinear, such as a substantially circular, guide path 81 for the fixation housing 80. The recess 78 extends transversely outward (or down) into the lower body portion 20b, and terminates prior to the bottom end 30 so as to define a base 83.

The fixation housing 80 can define any shape as desired, and in accordance with the illustrated embodiment is substantially annular and fits within the recess 78 such that a lower housing surface 85 of the fixation housing 80 can rest on the base 83. The fixation housing 80 defines an upper housing surface 87 that can rest against the upper end 26 of the upper body portion 28a when the body portions 28a and 28b are attached. The fixation housing 80 defines an inner cylindrical surface 80a that can bear against the outer surface 84a of the hub 84, and an outer surface 80b that can bear against the outer perimeter 91 of the recess 78. The fixation housing 80 can carry an engagement member 75 configured to operably couple to an engagement member 155 of the actuation tool 104 so as to iterate the fixation assembly between the first retracted position and the second extended position. For instance, the engagement member 75 can be configured as a plurality of teeth 53 that project out from the outer surface 80b, such that the fixation housing 80 can be configured as a worm wheel that receive a force from a worm gear of the actuation instrument 104 so as to drive the fixation assembly 22 from the retracted position to the extended position.

The fixation assembly 22 further includes the upper and lower fixation members 38 and 39 that are supported by the fixation housing 80. In particular, each of the upper and lower fixation members 38 and 39 can be provided as a pin having a proximal end 92 fastened to fixation housing 80, for instance at the upper and lower surfaces 87 and 85, respectively, an opposed distal end 93 that defines a tapered tip, and an intermediate portion 94 that extends between the proximal end 92 and the distal end 93. The intermediate portion 94 and the distal end 93 of each of the fixation members 38 and 39 can extend along the fixation housing 80 and can further be detached form the fixation housing 80, such that the fixation members 38 and 39 are only attached to the fixation housing 39 at their proximal ends 92. The upper and lower fixation members 38 and 39 can be substantially arc-shaped so as to extend along the respective upper and lower surfaces 87 and 85, and can be substantially circumferentially in-line with each other along the respective upper and lower surfaces 87 and 85.

When the fixation assembly 22 is in the first retracted position, the distal ends 93 of the fixation members 38 and 39 can extend into the leading ends 64a and 65a. The distal ends 93 can be beveled so as to facilitate insertion into, along, and through the respective channels 64 and 65 as the fixation housing 80 is rotated along the guide path 81 of the annular track 79 about the central transverse axis TT along a select rotational direction R3.

Figure 6A:
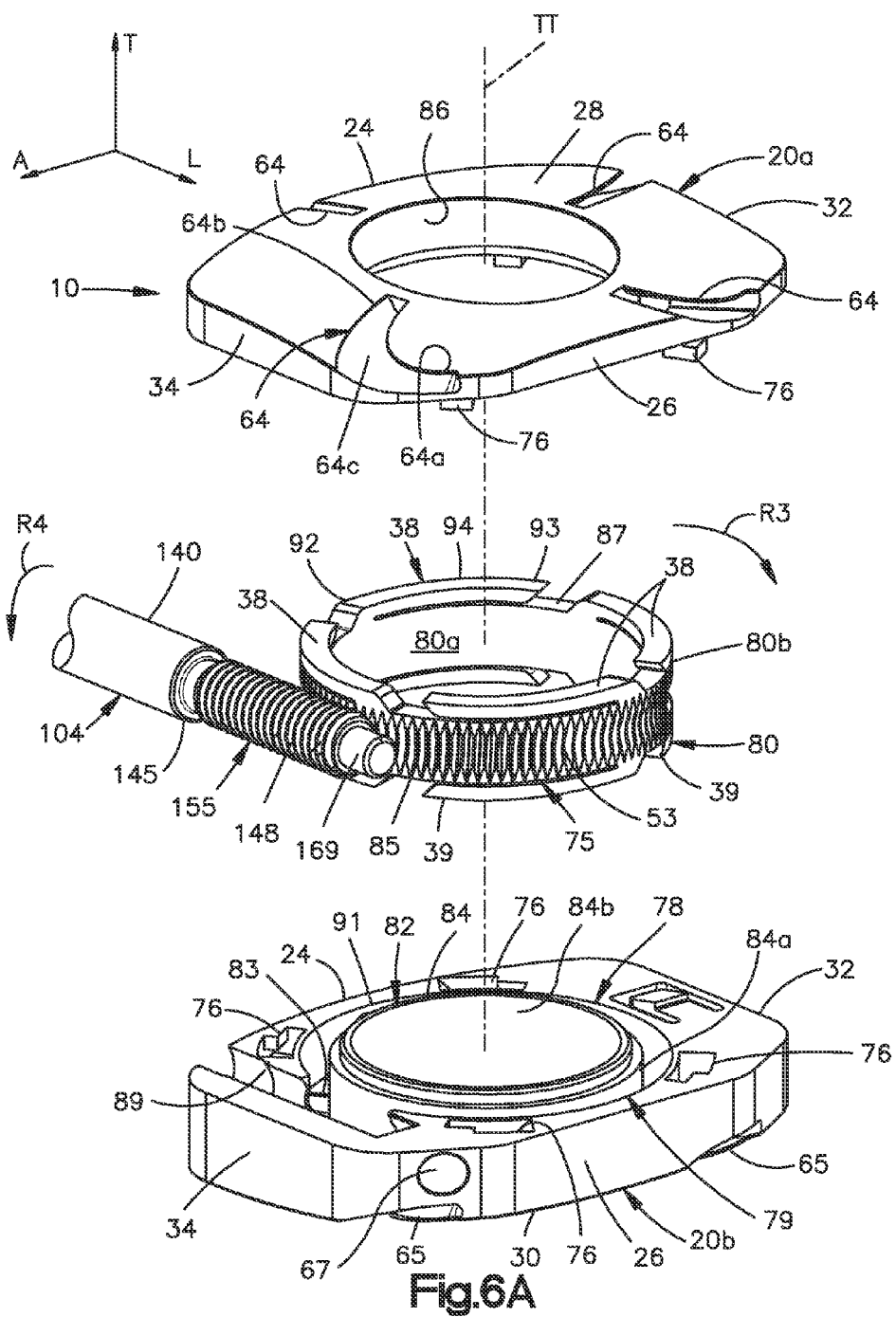
FIG. 6A is an exploded perspective view of a portion of the implant assembly illustrated in FIG. 2A, showing the actuation tool operatively coupled to the fixation assembly, and showing the implant in the first retracted position.
Figure 6B:
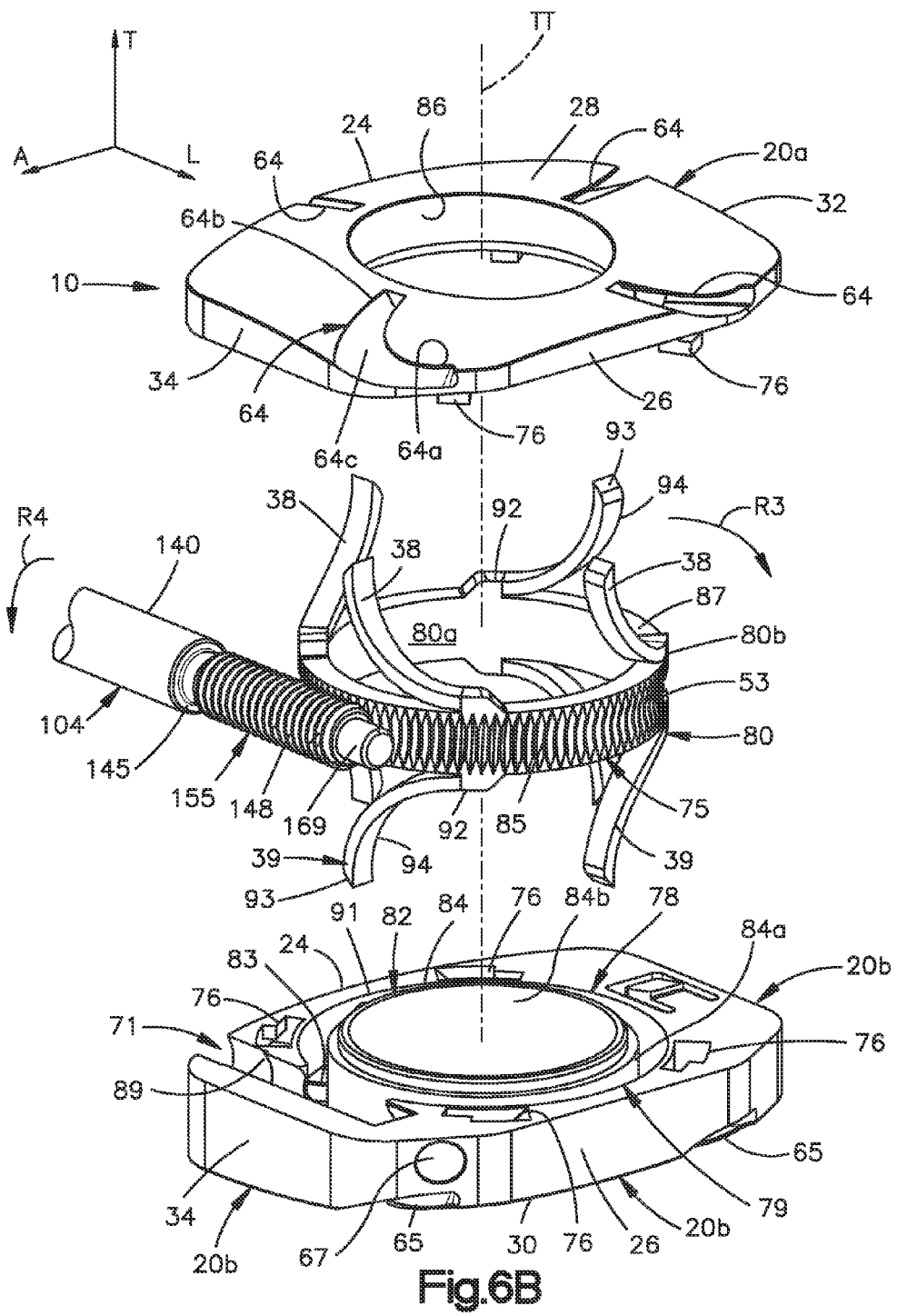
FIG. 6B is an exploded perspective view of a portion of the implant assembly similar to FIG. 6A, but showing the implant in the second extended position.
Figure 7A:
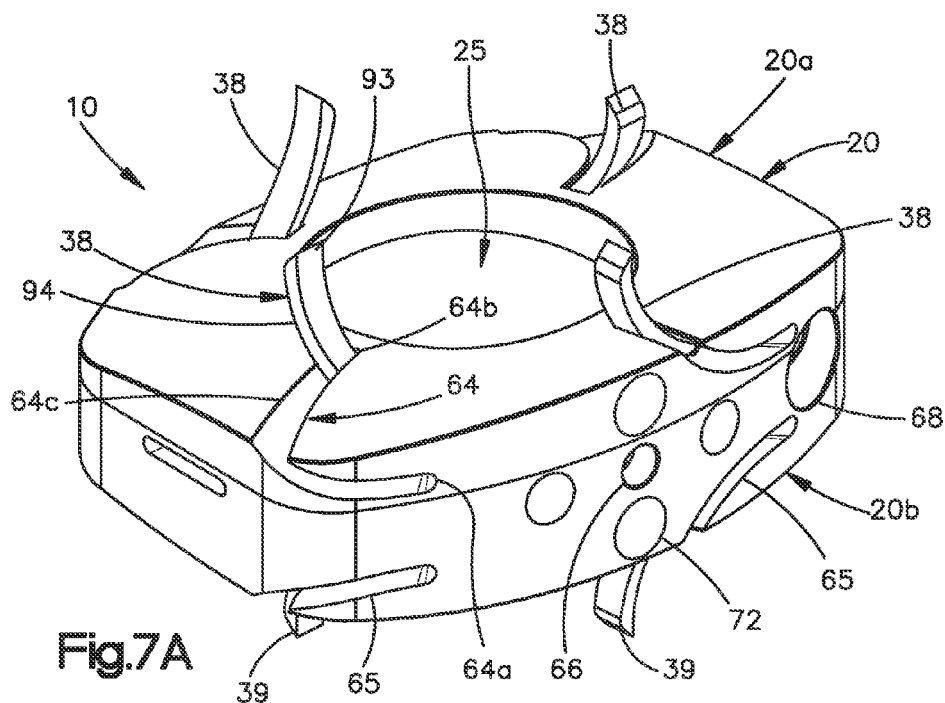
FIG. 7A is a top perspective view of the intervertebral implant illustrated in FIG. 2A, shown in the second extended position.
Figure 7B:
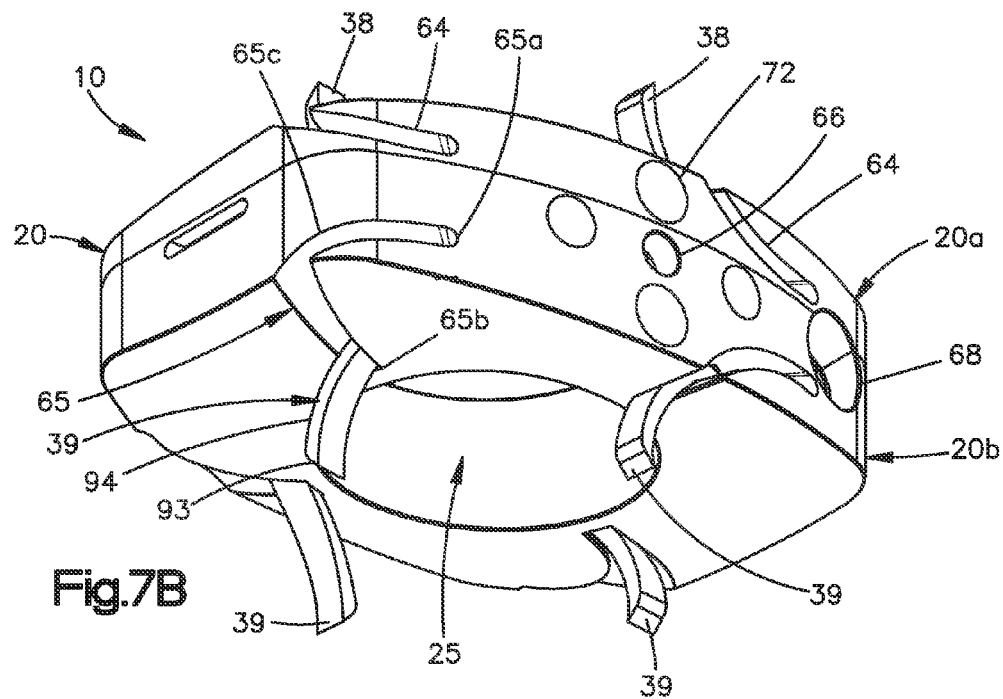
FIG. 7B is a bottom perspective view of the intervertebral implant illustrated in FIG. 7A.

For instance, referring now to FIGS. 2A and 6A-B, the actuation tool 104 is configured to be operably coupled to the fixation assembly 22, and in particular the fixation housing 80, such that an engagement member 155 of the actuation tool 104 mates with the engagement member 75 of the fixation assembly 22 so as to drive the fixation assembly 22 from the first retracted position into the second extended position. In accordance with the illustrated embodiment, the second attachment location 68 is configured as a channel 71 that extends into the front end 24 of the implant body 20 at a location adjacent to the fixation housing 80. The actuation tool 104 includes a shaft 140 that is longitudinally elongate along a central longitudinal axis 142, a handle 144 extending proximally from the shaft 140, and an engagement member 155 extending distally from the shaft 140. The engagement member 155 can be configured as a gear, such as a worm gear 148, that extends centrally along the longitudinal axis 142 and is configured to mate with the teeth 77 of the fixation housing 80, such that rotation of the actuation tool 104 about the central longitudinal axis 142 in a first rotational direction R4 causes the fixation housing 80 to rotate about the central transverse axis TT along the rotational direction R3, which further causes the proximal ends 92 of the fixation members 38 and 39 to travel along the circular guide path 81. Thus the actuation tool 104 rotates about an axis that is substantially perpendicular to the axis about which the fixation housing 80 rotates.

Referring also to FIGS. 7A-D, during operation, the implant 10 is inserted into the intervertebral space in the manner described above while the fixation assembly 22 is in the first retracted position, at which point the insertion tool 102 can be removed from the implant 10 prior to attaching the actuation tool 104 to the implant 10. Alternatively, if the handle 144 of the actuation tool 104 does not interfere with the insertion tool 102 during operation, the insertion tool 102 can remain attached to the implant 10 during operation of the actuation tool 104. Thus, it should be appreciated that the actuation tool 104 can have any length as desired, such that the handle 144 can be disposed proximal or distal with respect to the proximal end 106 of the insertion tool 102.

The actuation tool 104 is attached to the implant 10 by inserting the engagement member 155 into the channel 71 that extends into the implant body 20 such that the worm gear 148 meshes with the teeth 77 of the fixation housing 80. For instance, the engagement member 155 can be inserted into the channel 71 until the worm gear 148 contacts the teeth 77, at which point the actuation tool 104 can be rotated along the first rotational direction R4, which causes the engagement member 155 to advance longitudinally distally in the channel 71 until the engagement member 155 abuts a stop member of the implant 10 so as to prevent further distal translation of the actuation tool 104. For instance, a distal end 169 of the actuation tool 104 can become seated in a recess 67 that extends into the rear end 26 of the implant body 20 so as to prevent further distal translation of the actuation tool 104. Alternatively or additionally, the actuation tool 104 can define a shoulder 145 that is configured to abut an outer wall 89 of a recessed region in the channel 71.

As a result, further rotation of the actuation tool 104 about the longitudinal axis 142 along the direction of R4 causes the worm gear 148 to apply a biasing force to the fixation housing 80, and in particular to the engagement member 75, that drives the fixation housing 80 to rotate about the transverse axis TT along the direction of R3 so as to iterate the fixation assembly 22 from the retracted position to the extended position. As the fixation housing 80 rotates along the direction of R3, the fixation members 38 and 39 travel along their respective channels 64 and 65 along a direction from the leading ends 64a and 65a toward the trailing ends 64b and 65b until the distal ends 93 extend out the channels 64 and 65 and into the adjacent vertebral body. In accordance with the illustrated embodiment, the fixation members 38 and 39 are oriented along a first direction (e.g., substantially horizontally) when the fixation assembly 22 is in the first retracted position, and the fixation members 38 and 39, for instance at the distal ends 93, are oriented along a second direction (e.g., substantially transversely) that is substantially perpendicular to the first direction when the fixation assembly 22 is in the extended position.

The fixation members 38 and 39 can be made of any suitable flexible material and can thus be guided by the respective trailing ends 64b and 65b substantially transversely into the adjacent vertebral bodies. In one embodiment, the fixation members 38 and 39 can be made from a shape-memory material such as Nitinol, such that the fixation members 38 and 39 are internally biased such that the distal ends 93 are oriented substantially transversely outward as they extend out of the implant body 20.

Once the fixation assembly 22 is in the extended position, rotation of the actuation tool 104 about the longitudinal axis 142 along a second rotational direction R6 opposite the rotational direction R4 causes the worm gear 148 to engage the teeth 77 of the actuator housing 80 so as to drive the actuation tool 104 proximally out of the channel 71 until the engagement member 155 disengages the engagement member 75 of the fixation housing 80. The actuation tool 104 can then be withdrawn proximally out of the channel 71, such that the implant 10 remains disposed in the intervertebral space in the extended position such that the fixation members 38 and 39 extend into the respective adjacent vertebral bodies.

While the engagement member 155 of the actuation tool 104 can be configured to directly mate with the teeth 77 of the fixation housing 80 so as to operably couple the actuation tool 104 to the fixation assembly 22 in the manner described above, it should be further appreciated that the engagement member 155 of the actuation tool 104 can be configured to indirectly mate with the teeth 77 so as to operably couple the actuation tool 104 to the fixation assembly 22. For instance, the fixation assembly 22 can include a force transfer member that is permanently disposed in the channel 71 and translatably fixed in the channel 71, and carries an actuator, such as a worm gear, that is operably coupled to the engagement member 75 of the fixation housing 80. The force transfer member can include any suitable coupling member configured to receive a rotational force from the actuation tool 104, as the actuation tool rotates along the first rotational direction R4, such that the force transfer member applies to the fixation housing 80 so as to iterate the fixation housing from the first retracted position to the second extended position.

Furthermore, as described above, it should be appreciated that the recess 78 can define any shape as desired. For instance, the recess 78 can be linear, and can thus define one or more linear tracks such that actuation of the fixation housing 80 causes the fixation members 38 and 39 to travel tangentially with respect to the fixation housing 80, and thus linearly in the respective track between the first retracted position and the second extended position.

In accordance with one embodiment, a vertebral fixation kit can include at least one such as a plurality of instrument assemblies 100 of the same or different sizes and shapes, and can alternatively or additionally include at least one such as a plurality of implants 10 of the same or different sizes and shapes. For instance, a vertebral fixation kit can include a plurality of implants 10 of different sizes and shapes suitable for different regions along the spine of a given patent, or different regions along the spine from patient-to-patient, and at least one instrument assembly 100 configured to insert at least one up to all of the implants 10 of the kit into the intervertebral space and to subsequently iterate the implants 10 from the first retracted position to the second extended position.

Although the invention has been described with reference to preferred embodiments or preferred methods, it is understood that the words which have been used herein are words of description and illustration, rather than words of limitation. For instance, it should be appreciated that while the intervertebral implant has been described herein as configured to fix to adjacent vertebral bodies, the implant can alternatively be inserted into a space between any bones or bone segments (e.g., fractured bone segments) as desired, and subsequently fixed to the adjacent bones or bone segments in the manner described herein. Furthermore, although the invention has been described herein with reference to particular structure, methods, and embodiments, the invention is not intended to be limited to the particulars disclosed herein, as the invention extends to all structures, methods and uses that are within the scope of the present invention. Unless otherwise indicated, the structure and features of various embodiments described herein can further be incorporated into the other embodiments described herein as desired. Accordingly, those skilled in the art will realize that the invention is intended to encompass all modifications and alternative arrangements included within the spirit and scope of the invention, for instance as set forth by the appended claims.

What is claimed is:

1. An intervertebral implant configured to be fixed in an intervertebral space defined by a superior vertebral body and a inferior vertebral body, the intervertebral implant comprising:
    an implant body sized to be inserted into the intervertebral space, the implant body defining superior and inferior vertebral facing surfaces that are spaced apart along a transverse direction, and the implant body further defining a superior curvilinear channel that is open at the superior vertebral facing surface, and an inferior curvilinear channel that is open at the inferior vertebral facing surface; and
    a fixation assembly carried by the implant body, the fixation assembly including a fixation housing extending along a substantially transverse axis that is aligned with the transverse direction, a superior vertebral fixation member carried by the housing and configured to travel in the superior channel, and an inferior vertebral fixation member carried by the housing and configured to travel in the inferior channel,
    wherein the fixation assembly is rotatable within the implant body about the substantially transverse axis from a retracted position to an extended position whereby the superior and inferior vertebral fixation members travel in the superior and inferior curvilinear channels respectively, so as to extend out from the superior and inferior surfaces, respectively.

2. The intervertebral implant as recited in claim 1, wherein the superior and inferior channels define respective leading ends that terminate in the implant body and opposed trailing ends that are open to the superior and inferior vertebral facing surfaces, respectively.

3. The intervertebral implant as recited in claim 2, wherein the superior and inferior curvilinear channels define respective curvilinear paths that extend from the respective leading ends to the trailing ends with respect to the transverse axis.

4. The intervertebral implant as recited in claim 1, wherein the fixation members are oriented along a first direction when the fixation assembly is in the retracted position, and are oriented along a second direction substantially perpendicular to the first direction when the fixation assembly is in the extended position.

5. The intervertebral implant as recited in claim 4, wherein the second direction is the transverse direction.

6. The intervertebral implant as recited in claim 1, wherein the fixation housing travels along a curvilinear guide path from the retracted position to the extended position.

7. The intervertebral implant as recited in claim 6, wherein the guide path is substantially circular.

8. The intervertebral implant as recited in claim 7, wherein the implant body defines a central hub and the fixation housing rotates about the central hub from the retracted position to the extended position.

9. The intervertebral implant as recited in claim 8, wherein the central hub is substantially annular.

10. The intervertebral implant as recited in claim 1, wherein the fixation members are flexible.

11. The intervertebral implant as recited in claim 1, wherein the fixation housing carries an engagement member configured to receive a biasing force from an actuation instrument that drives the fixation housing so as to iterate the fixation assembly from the retracted position to the extended position.

12. The intervertebral implant as recited in claim 11, wherein the actuation instrument comprises a plurality of teeth.

13. The intervertebral implant as recited in claim 12, wherein the fixation housing comprises a worm wheel.

14. The intervertebral implant as recited in claim 1, wherein the fixation housing has an upper end and a lower end spaced from the upper end along the transverse axis, wherein the superior vertebral fixation member is carried by the upper end of the housing and the inferior vertebral fixation member is carried by the lower end of the housing.

15. The intervertebral implant as recited in claim 14, wherein the fixation housing defines a bore that extends from the upper end to the lower end along the transverse axis.

16. The intervertebral implant as recited in claim 14, wherein the fixation housing defines an inner circumferential surface that extends from an upper end of the housing to a lower end of the housing, and an outer surface spaced from the inner circumferential surface along a radial direction that is substantially perpendicular to the transverse axis.

17. The intervertebral implant as recited in claim 16, wherein the fixation housing is curvilinear with respect to the transverse axis.

18. The intervertebral implant as recited in claim 1, wherein the fixation housing, at least a portion of the superior vertebral fixation member, and at least a portion of inferior vertebral fixation member are integral.

19. An implant assembly comprising:
an implant configured to be fixed in an intervertebral space defined by a first vertebral body and a second vertebral body, the intervertebral implant including:
an implant body sized to be inserted into the intervertebral space, the implant body defining opposed vertebral facing surfaces, and at least one channel that is open at one of the vertebral facing surfaces; and
a fixation assembly carried by the implant body, the fixation assembly including a fixation housing and a vertebral fixation member carried by the fixation housing and configured to travel in the at least one channel; and
an instrument assembly comprising an actuation instrument configured to rotate along a first axis so as to apply a biasing force against the fixation housing that drives the fixation housing to rotate along a rotation direction about a second axis that is substantially perpendicular to the first axis, wherein rotation of the fixation housing rotates the vertebral fixation member along the rotational direction through the at least one channel.

20. The implant assembly as recited in claim 19, wherein the first and second vertebral bodies are spaced apart along the second axis.

21. The implant assembly as recited in claim 19, wherein the actuation instrument comprises a worm gear that applies the biasing force to the fixation housing as the actuation instrument rotates along the first axis.

22. The implant assembly as recited in claim 19, wherein the instrument assembly further comprises an insertion tool separate from the actuation instrument that is configured to grip the implant so as to insert the implant into the intervertebral space.

23. The implant assembly as recited in claim 22, wherein the implant defines an attachment location and a plurality of brace locations disposed adjacent the attachment location, and the insertion tool comprises both an attachment member configured to engage the implant at the attachment location and a plurality of brace members configured to engage the implant at the brace locations.

24. The implant assembly as recited in claim 23, wherein the insertion tool comprises an actuator configured to translate the attachment member away from the implant relative to the brace members once the attachment member has engaged the implant at the attachment location.

25. The implant assembly as recited in claim 24, wherein the attachment location comprises an aperture extending into the implant body, and the attachment member comprises a projection configured to be press-fit in the aperture.

26. An intervertebral implant configured to be fixed in an intervertebral space defined by a first vertebral body and a second vertebral body, the intervertebral implant comprising:
an implant body sized to be inserted into the intervertebral space, the implant body defining first and second vertebral facing surfaces that are spaced apart along a transverse direction, and the implant body further defining a first channel that is open at the first facing surface, and a second channel that is open at the second vertebral facing surface; and
a fixation assembly carried by the implant body, the fixation assembly including a fixation housing having a first end and a second end spaced from the first end along a transverse axis that is substantially aligned with the transverse direction, the fixation assembly including a first vertebral fixation member carried by the first end of the housing and configured to travel in the first channel, and a second vertebral fixation member carried by the second end of the housing and configured to travel in the second channel, wherein the entire fixation assembly is rotatable within the implant body about the transverse axis from a retracted position to an extended position whereby the first and second vertebral fixation members travel in the first and second channels, respectively, so as to extend out from the first and second vertebral facing surfaces, respectively.

27. The intervertebral implant as recited in claim 26, wherein the fixation housing defines an inner circumferential surface extending from the first end of the housing to the second end of the housing along the transverse axis, and an outer circumferential surface spaced from the inner circumferential inner surface along a radial direction that is substantially perpendicular to the transverse axis.

28. The intervertebral implant as recited in claim 27, wherein the fixation housing travels along a circular guide path from the retracted position to the extended position.

29. The intervertebral implant as recited in claim 27, wherein the implant body defines a central hub extending along at least a portion of the inner circumferential surface, such that the fixation housing is rotatable about the central hub.

30. The intervertebral implant as recited in claim 29, wherein the central hub is substantially annular.

* * * * *